(12) United States Patent
Hakozaki et al.

(10) Patent No.: US 11,571,379 B2
(45) Date of Patent: Feb. 7, 2023

(54) SKIN CARE COMPOSITION

(71) Applicant: The Procter & Gamble Company, Cincinnati, OH (US)

(72) Inventors: Tomohiro Hakozaki, Cincinnati, OH (US); Bin Fang Deyer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/155,151

(22) Filed: Jan. 22, 2021

(65) Prior Publication Data

US 2021/0228469 A1 Jul. 29, 2021

Related U.S. Application Data

(60) Provisional application No. 62/965,189, filed on Jan. 24, 2020.

(51) Int. Cl.
*A61K 8/73* (2006.01)
*A61Q 19/00* (2006.01)
*A61K 8/06* (2006.01)
*A61K 8/67* (2006.01)

(52) U.S. Cl.
CPC .............. *A61K 8/73* (2013.01); *A61K 8/062* (2013.01); *A61K 8/671* (2013.01); *A61K 8/675* (2013.01); *A61K 8/678* (2013.01); *A61Q 19/00* (2013.01)

(58) Field of Classification Search
None
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 5,011,681 A | 4/1991 | Ciotti et al. |
| 5,830,499 A | 11/1998 | Bouwstra |
| 5,872,112 A | 2/1999 | Blank |
| 5,939,082 A | 8/1999 | Oblong et al. |
| 5,972,359 A | 10/1999 | Sine et al. |
| 6,174,533 B1 | 1/2001 | Sanogueira, Jr. et al. |

(Continued)

FOREIGN PATENT DOCUMENTS

| | | |
|---|---|---|
| CN | 103655313 A | 3/2014 |
| CN | 104027265 A | 9/2014 |

(Continued)

OTHER PUBLICATIONS

All Office Actions; U.S. Appl. No. 17/549,980, filed Dec. 14, 2021.

(Continued)

*Primary Examiner* — Dominic Lazaro
(74) *Attorney, Agent, or Firm* — Alexandra S. Anoff

(57) ABSTRACT

Methods and compositions for improving the appearance of skin are provided. The methods and compositions are especially suited for improving sallow-looking skin by enhancing bilirubin degradation in skin. The methods and compositions herein utilize one or more sucrose esters, which demonstrate a surprising ability to reduce bilirubin levels. The method involves applying a skin care composition containing an effective amount of a sucrose ester to a target portion of skin where a reduction in bilirubin level is desired.

17 Claims, 4 Drawing Sheets

(56) References Cited

U.S. PATENT DOCUMENTS

| | | | |
|---|---|---|---|
| 6,238,678 | B1 | 5/2001 | Oblong et al. |
| H2013 | H | 2/2002 | Boyd et al. |
| 6,492,326 | B1 | 12/2002 | Robinson |
| 6,524,598 | B2 | 2/2003 | Sunkel et al. |
| 6,696,049 | B2 | 2/2004 | Vatter |
| 9,446,265 | B2 | 9/2016 | Jansen et al. |
| 9,757,317 | B2 | 9/2017 | Laughlin et al. |
| 9,795,552 | B2 * | 10/2017 | Tanner .................. A61K 8/89 |
| 9,833,398 | B2 | 12/2017 | Hakozaki et al. |
| 10,660,838 | B2 | 5/2020 | Hakozaki et al. |
| 10,874,600 | B2 | 12/2020 | Hakozaki et al. |
| 2002/0022040 | A1 | 2/2002 | Robinson et al. |
| 2003/0049212 | A1 | 3/2003 | Robinson et al. |
| 2004/0175347 | A1 | 9/2004 | Bissett |
| 2005/0220726 | A1 | 10/2005 | Pauly et al. |
| 2006/0165735 | A1 * | 7/2006 | Abril .................. C09K 23/00 424/195.17 |
| 2006/0275237 | A1 | 12/2006 | Bissett |
| 2007/0196344 | A1 | 8/2007 | Osborne et al. |
| 2008/0181956 | A1 | 7/2008 | Ha et al. |
| 2008/0206373 | A1 | 8/2008 | Millikin et al. |
| 2010/0092408 | A1 | 4/2010 | Breyfogle et al. |
| 2010/0189669 | A1 | 7/2010 | Hakozaki |
| 2010/0239510 | A1 | 9/2010 | Ha et al. |
| 2010/0272667 | A1 | 10/2010 | Kyte, III et al. |
| 2011/0097286 | A1 | 4/2011 | Swanson |
| 2011/0262025 | A1 | 10/2011 | Jarrold et al. |
| 2012/0128603 | A1 | 5/2012 | Tanaka |
| 2012/0128683 | A1 | 5/2012 | Shantha |
| 2012/0148510 | A1 | 6/2012 | Hakozaki et al. |
| 2012/0148515 | A1 | 6/2012 | Hakozaki et al. |
| 2012/0156146 | A1 | 6/2012 | Hakozaki et al. |
| 2012/0197016 | A1 | 8/2012 | Laughlin, II et al. |
| 2013/0022557 | A1 | 1/2013 | Swanson et al. |
| 2014/0271506 | A1 | 9/2014 | Laughlin, II et al. |
| 2014/0328775 | A1 | 11/2014 | Laughlin, II et al. |
| 2015/0196464 | A1 | 7/2015 | Jansen et al. |
| 2016/0128924 | A1 | 5/2016 | Lee et al. |
| 2019/0380945 | A1 | 12/2019 | Hakozaki et al. |
| 2020/0009123 | A1 | 1/2020 | Hakozaki et al. |
| 2020/0178881 | A1 | 6/2020 | Purwar et al. |
| 2020/0253851 | A1 | 8/2020 | Hakozaki et al. |
| 2020/0405614 | A1 | 12/2020 | Hakozaki |
| 2020/0405621 | A1 | 12/2020 | Hakozaki |
| 2020/0405622 | A1 | 12/2020 | Paufique |

FOREIGN PATENT DOCUMENTS

| | | | | |
|---|---|---|---|---|
| CN | 105560158 | A | 5/2016 | |
| CN | 105662908 | A | 6/2016 | |
| CN | 107595756 | A | 1/2018 | |
| EP | 1216625 | A1 | 6/2002 | |
| EP | 1842530 | A1 * | 10/2007 | ............... A61K 8/60 |
| EP | 1842530 | A1 | 10/2007 | |
| WO | 9947141 | A1 | 9/1999 | |
| WO | 2006040048 | A1 | 4/2006 | |
| WO | 2011074143 | A1 | 6/2011 | |
| WO | 2012068357 | A2 | 5/2012 | |

OTHER PUBLICATIONS

All Office Actions; U.S. Appl. No. 17/549,989, filed Dec. 14, 2021.
U.S. Unpublished U.S. Appl. No. 17/549,989, filed Dec. 14, 2021, to Matthew Clair Ehrman et al.
U.S. Unpublished U.S. Appl. No. 17/549,980, filed Dec. 14, 2021, to Tomohiro (NMN) Hakozaki et al.
"Sensitive Multi-Benefit Integral Care for Sensitive Skin", Mintel, Retrieved from : Http://www.gndp.com.
15712M PCT Search Report and Written Opinion for PCT/US2021/014496 dated May 19, 2021.
Boulier et al., "New Formulations containing a blend of Sucrose Laurates", Sensient Cosmetic Technology, vol. 535, Nov. 1, 2008, 4 pages.
Miyamoto et al. Skin Res Technol, "Development of a Digital Imaging System for Objective Measurement of Hyperpigmented Spots on the Face;" Skin Res Technol 2002; 8:227-35.
Niacinamide—Mechanisms of Action and Its Topical Use in Dermatology, Skin Pharmacol Physiol 2014, Jun. 27, 2014, pp. 311-315.
The use of gene arrays and corresponding connectivity mapping (cMap) to identify novel anti-ageing ingredients, International Journal of Cosmetic Science (2015), vol. 37 issue S1, p. 9-14.
Vermeire et al., "Sucrose Laurate Gels as a Percutaneous Delivery System for Oestradiol in Rabbits", Journal of Pharmacy and Pharmacology, vol. 48, 1996, pp. 463-467.
Mitsubishi—Kagaku Foods Corporation; Anonymous: Ryoto Sugar Ester (Food Grade), Internet Citation, XP002557521, Retrieved from the internet: URL: http://web.archive.org/web20080524191629/ http://www.mfc.co.jp/english/seihin.htm; retrieved on Nov. 26, 2009; pp. 01.

* cited by examiner

SKIN CARE COMPOSITION

FIELD

The present disclosure is directed generally to skin care compositions for treating skin tone conditions. More specifically, the present disclosure is directed to a method that utilizes an effective amount of a sucrose ester to provide a bilirubin degradation benefit.

BACKGROUND

Sallow or yellow-looking skin is commonly associated with poor health or old age and can be influenced by a variety of physiological and environmental factors. For example, it is well-known that yellow- or sallow-looking skin can be caused by a buildup of yellow pigment known as bilirubin. For example, bilirubin is responsible for the yellowish coloring in skin associated with bruising or jaundice. Bilirubin is produced as a result of the catabolic breakdown of heme in red blood cells, which occurs when old or damaged cells are cleared from the body. Typically, bilirubin is processed by the liver and then excreted from the body as waste. Thus, it would be desirable to provide a way to improve the appearance of yellow- or sallow-looking skin associated with bilirubin buildup.

One known method of reducing bilirubin levels in skin is through light therapy (a.k.a. photo therapy). Certain wavelengths of light react with bilirubin and convert it to a form that is more easily processed and removed by the body. Light therapy is one of the common forms of treating undesirably high bilirubin levels in newborn babies (i.e., hyperbilirubinemia). However, light therapy can require spending a significant amount of time (e.g., 12-72 hours) under an artificial light source in an away-from-home environment (e.g., hospital), which may be undesirable for many people suffering from such conditions. Accordingly, it would be desirable to provide a more convenient method of degrading bilirubin in skin to improve the appearance of a sallow-looking skin.

Cosmetic compositions claiming to improve the degradation of bilirubin are commercially available, but many, if not all, such products are intended for use in improving the appearance of undereye dark circles. For example, Eyedeline™ marine ingredient brand cosmetic eye care product from Lipotec purports to improve the appearance of undereye dark circles by enhancing bilirubin degradation, among other things. Truthinaging.com discloses that cosmetic and beauty products comprising N-hydroxysuccinimide, such as the eye serum product available from AQ Skin Solution, activate the elimination of blood originated pigments such as bilirubin, which contribute to the appearance of undereye dark circles. In another example, a botanical ingredient obtained from the White Bird of Paradise flower (commercially available as Vivillume™ from Lonza, N.J.) is claimed to degrade bilirubin. Cosmetic products sold by the Avani company (Spain) for treating undereye dark circles are advertised as including Vivillume™. Eye treatment products are formulated to treat the relatively small areas of skin present in the periorbital region of the face, and thus may not be suitable for treating larger areas of skin to address appearance issues associated with the presence of bilirubin in the skin (e.g., sallow-looking skin and/or uneven skin tone). In addition, at least some people who suffer from sallow-looking skin also want a skin care product that treats other cosmetic skin conditions such as fine lines, wrinkles, hyperpigmented spots, and/or dull skin.

Accordingly, it would be desirable to provide a personal care composition that improves the appearance of sallow-looking skin by applying a composition to skin that is capable of improving bilirubin degradation. It would also be desirable to provide a skin care composition that provides a skin care benefit in addition to a bilirubin degradation benefit.

SUMMARY

A method of improving the appearance of skin and/or degrading bilirubin in skin is described herein. The method comprises identifying a target portion of skin on a person where a reduction in bilirubin is desired, and applying a composition comprising an effective amount of a sucrose ester selected from sucrose laurate, sucrose dilaurate, and/or sucrose trilaurate to the target portion of skin during a treatment period, wherein the effective amount of sucrose ester reduces bilirubin level during a treatment period.

DETAILED DESCRIPTION

Figure 1:
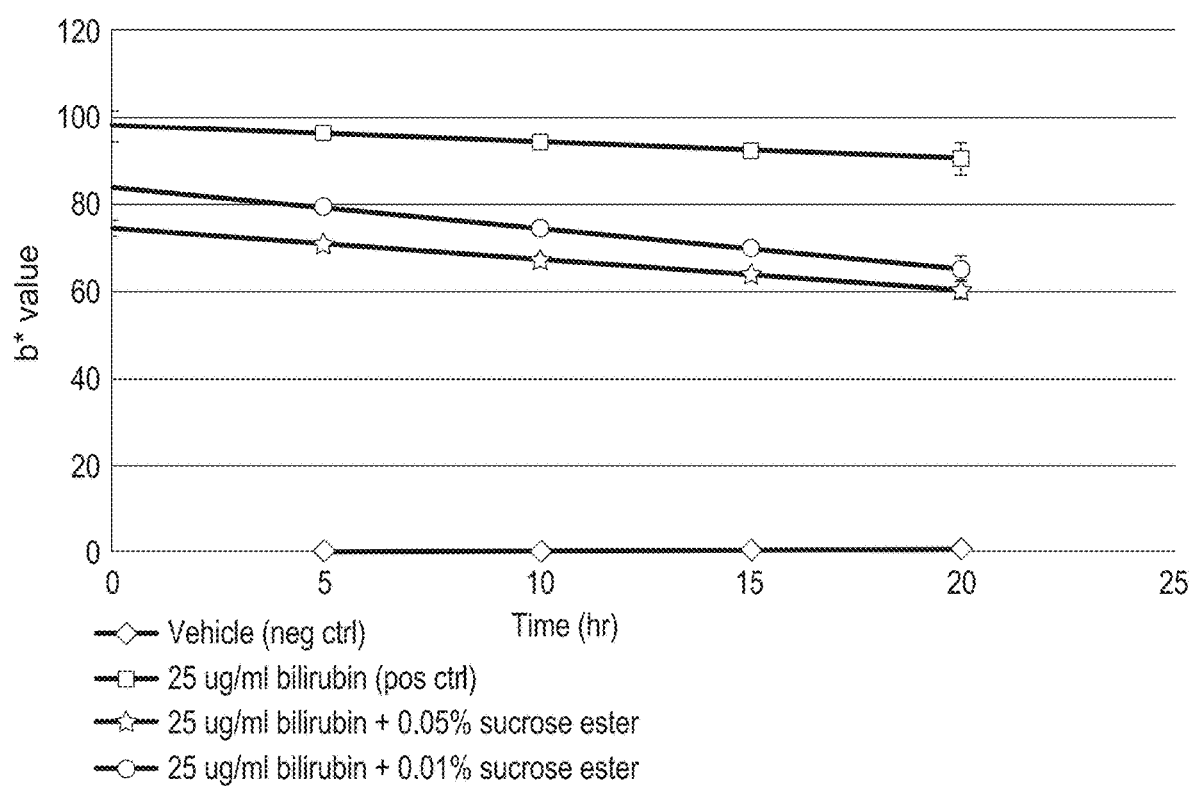
FIG. 1 illustrates the in vitro effects of a sucrose ester on b* value.

The drawbacks associated with the presence and/or buildup of bilirubin in skin are well known, but conventional treatments for reducing bilirubin levels in skin, such as light therapy, may not suitable for all users. Prior to the present discovery, it was not known that certain sucrose esters, such as sucrose laurate, sucrose dilaurate, and sucrose trilaurate, can be used to degrade bilirubin. Surprisingly, it has now been found that skin care compositions containing a sucrose ester can be used to improve the appearance of sallow-looking skin and/or uneven skin tone.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive and combinable to form narrower ranges not explicitly disclosed. For example, delineated upper and lower range limits are interchangeable to create further ranges.

The compositions of the present invention can comprise, consist essentially of, or consist of, the essential components as well as optional ingredients described herein. As used herein, "consisting essentially of" means that the composition or component may only include additional ingredients that do not materially alter the basic and novel characteristics of the claimed composition or method. As used in the description and the appended claims, the singular forms "a", "an", and "the" are intended to include the plural forms as well, unless the context clearly indicates otherwise.

Definitions

"About" modifies a particular value by referring to a range equal to plus or minus twenty percent (+/−20%) or less (e.g., less than 15%, 10%, or even less than 5%) of the stated value.

"Agent" refers to a material, as well any component thereof, intended to provide a particular benefit or function. For example, an emollient agent is a material intended to provide an emolliency benefit to skin (e.g., a fatty alcohol), and a thickening agent is a material generally intended to increase the viscosity of a composition.

"Apply" or "application", as used in reference to a composition, means to apply or spread the compositions of the present invention onto a human skin surface such as the epidermis.

"Bilirubin" means the compound identified as CAS No. 635-65-4 and having the chemical formula $C_{33}H_{36}N_4O_6$ and the following structure:

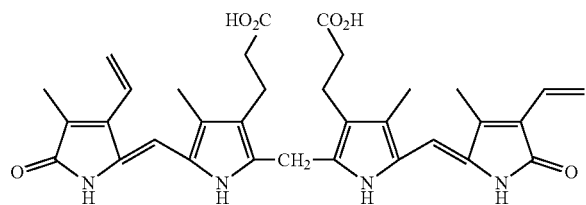

"Cosmetic composition" means a composition comprising a cosmetic agent such as the sucrose esters described herein. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Derivative," herein, means amide, ether, ester, amino, carboxyl, acetyl, and/or alcohol derivatives of a given compound.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of sucrose ester is an amount sufficient to reduce bilirubin level.

"Improve the appearance of" means providing a measurable, desirable change or benefit in the skin appearance of a person, which may be quantified, for example, by a decrease in b* value. Exemplary methods for determining improvements in appearance are described in more detail below.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Safe and effective amount" means an effective amount of an ingredient that is low enough to avoid serious side effects (within the scope of sound medical judgment).

"Sallow," when referring to the appearance of skin herein, means an unusual and/or undesirable yellow or pale skin tone, with regard to a particular individual, which is commonly associated with an unhealthy state. Sallow-appearing skin can be diagnosed objectively (e.g., with a color value such as L* or b*) or subjectively (e.g., by a skin care professional or via self-diagnosis by a consumer).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone" means the overall appearance of basal skin color or color evenness. Skin tone is typically characterized over a larger area of the skin, which is generally more than 100 mm², up to and including the entirety of the facial skin or other bodily skin surface (e.g., arms, legs, back, hands, neck, chest and abdomen). Skin tone can be measured by image analysis. One measure of skin tone is lightness, which can be measured by the L* coordinate in the L*a*b* color space (International Commission on Illumination). Chromophore mapping such as melanin and/or bilirubin mapping and may also be used as an indicator of skin tone. Mean melanin and/or bilirubin may be calculated from the chromophore map data. Additionally, skin tone can be correlated to melanin and/or bilirubin evenness (e.g., standard deviation) which also may be calculated from the chromophore map data.

"Treatment period," as used herein, means the length of time and/or frequency that a material or composition is applied to a target skin surface.

Composition

The compositions herein contain an effective amount of a sucrose ester disposed in a dermatologically acceptable carrier and are intended for topical application to human skin. The amount of sucrose ester should be sufficient to demonstrate an in vitro bilirubin degradation benefit and/or improve the appearance of sallow looking skin after a suitable course of treatment (e.g., 2, 4 or 8 weeks). The compositions herein can also treat other skin conditions and may optionally include one or more additional skin actives or other ingredients of the type commonly included in topical skin care compositions. The skin care compositions herein can be made using conventional methods of combining skin care composition ingredients.

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

Sucrose Ester

The compositions herein include an effective amount of a sucrose ester selected from sucrose laurate, sucrose dilaurate, sucrose trilaurate, derivatives of these, and combinations thereof. As used herein, "sucrose laurate" means a compound having the formula $C_{24}H_{44}O_{12}$ and CAS #25339-99-5; "sucrose dilaurate" means a compound having the formula $C_{36}H_{66}O_{13}$ and CAS #25915-57-5; and "sucrose trilaurate" means a compound having the formula $C_{48}H_{88}O_{14}$ and CAS #94031-23-9. The sucrose ester may be present at 0.0001% to 15% (e.g., 0.0002% to 10%, 0.001% to 15%, 0.025% to 10%, 0.05% to 7%, 0.05% to 5%, or even 0.1% to 3%) by weight of the total composition. In some instances, the sucrose ester may be a single sucrose ester (e.g., 100% sucrose laurate, sucrose dilaurate, sucrose trilaurate, or a derivative of these) or a blend of two or three sucrose esters, wherein the two or more sucrose esters are present at a ratio of any one sucrose ester to another of 1:10 to 1:1 (e.g., 1:7, 1:5, 1:3, or 1:2). In some instances, the sucrose ester may be a blend of sucrose laurate and sucrose dilaurate, wherein sucrose laurate is present at 50% to 80%, by weight, of the sucrose ester, and sucrose dilaurate is present at 20% to 45%, by weight, of the sucrose ester. Alternatively, the sucrose ester may be a blend of sucrose laurate, sucrose dilaurate, and sucrose trilaurate, wherein sucrose dilaurate is present at 35% or more, by weight, of the sucrose ester. A suitable example of a sucrose ester for use herein is BC10034 from BASF, which is a blend of sucrose laurate and sucrose dilaurate. The BC10034 sucrose ester material can have a ratio of sucrose laurate to sucrose dilaurate ranging from 3:1 to 3:2.

Dermatologically Acceptable Carrier

The bilirubin degrading compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the sucrose ester can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol. (e.g., molecular weight of 200 to 600 g/mole), polypropylene glycol (e.g., molecular weight of 425 to 2025 g/mole), glycerol, butylene 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Other Optional Ingredients.

The compositions herein may include one or more optional ingredients known for use in topical skin care compositions, provided that the optional components do not unacceptably alter the desired benefits of the composition.

The additional ingredients should be suitable for use in contact with human skin tissue without undue toxicity, incompatibility, instability, allergic response, and the like. The optional components, when present, may be included at an amount of about 0.001% to 50% (e.g., 0.01% to 40%, 0.1% to 30%, 0.5% to 20%, or 1% to 10%), by weight of the composition. Some nonlimiting examples of additional ingredients include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunscreen agents, sunless tanning agents, lubricants, anti-acne agents, anti-cellulite agents, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some nonlimiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Rheology Modifiers

The compositions herein may include 0.1% to 5% of a rheology modifier (e.g., thickening agent) to provide the composition with suitable rheological and skin feels properties. Some non-limiting examples of thickening agents include crosslinked polyacrylate polymers, polyacrylamide polymers, polysaccharides, gums and mixtures thereof. In a particularly suitable example, the composition may include a superabsorbent polymer thickening agent such as sodium polyacrylate, starch grafted sodium polyacrylate, or a combination of these. Some non-limiting examples of superabsorbent polymer thickeners are described in, for example, U.S. Pat. No. 9,795,552.

Some consumers find compositions that use silicone fluids as conditioning agents to be undesirably greasy or heavy feeling. Thus, it may be desirable to provide a composition that is free of or substantially free of silicone fluid. It may also be desirable to tailor a superabsorbent polymer thickener to provide the composition with a light, airy feel, for example, by adjusting the amount of water in the composition, the water-to-oil ratio (e.g., between 12:1 and 1:1), and/or the ratio of water to thickener or oil to thickener.

Emulsifiers

When the composition is in the form of an emulsion, it may contain an emulsifier. Emulsifiers may be nonionic, anionic or cationic. Suitable emulsifiers are disclosed in, for example, U.S. Pat. Nos. 3,755,560, 4,421,769, U.S. Publication No. 2006/0275237 and McCutcheon's Detergents and Emulsifiers, North American Edition, pages 317-324 (1986). Suitable emulsions may have a wide range of viscosities, depending on the desired product form.

When including optional ingredients in the compositions herein, it may be desirable to select ingredients that do not form complexes or otherwise undesirably interact with other ingredients in the composition, especially pH sensitive ingredients like niacinamide, salicylates and peptides (e.g., palmitoyl-lysine-threonine (pal-KT) or palmitoyl-lysine-threonine-threonine-lysine-serine (pal-KTTKS). In particular, the additional ingredients should not undesirably affect the ability of the sucrose ester to degrade bilirubin. In some instances, it may be desirable to select skin care actives that function via different biological pathways so that the actives do not interfere with one another, which could reduce the efficacy of both agents.

Method of Use

The present method includes identifying a target portion of skin on a person in need of treatment and applying a composition comprising an effective amount of one or more of the sucrose esters described herein, and optionally one or more additional skin care agents, to the target portion of skin during a treatment period. The target portion of skin may be on a facial skin surface such as the forehead, perioral, chin, periorbital, nose, and/or cheek) or another part of the body (e.g., hands, arms, legs, back, chest). The person in need of treatment can be one who exhibits an undesirable level of bilirubin in their skin and/or exhibits another undesirable cosmetic skin condition. Bilirubin level may be determined according to any suitable method known in the art. For example, bilirubin level may be determined by a blood sample analysis. In another example, an undesirable bilirubin level may be indicated if the target portion of skin has a b* value greater than a predetermined threshold level corresponding to an undesirably high bilirubin level. The b* value may be determined according to the color imaging method described in more detail below. In some instances, a person may be identified as being in need of treatment when their skin exhibits a yellow or sallow appearance and/or the person has an uneven skin tone. In another example, a person in need of treatment may be identified when an undesirable level of yellowness is determined to be present in a target portion of skin by an expert (e.g., dermatologist or cosmetologist). The person in need of treatment may also identify the target portion of skin when bruising is present. In some instances, a target portion of skin may not appear to be suffering from a buildup of bilirubin, but a user (e.g., a person suffering from or prone to jaundice or bruising) may still wish to treat the target portion of skin as a preventative measure (e.g., if the person is prone to conditions that cause bilirubin buildup such as jaundice).

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions improve the appearance of skin by reducing bilirubin level, for example, as demonstrated by a reduction in b* of at least 5% (e.g., at least 10%, 15%, 20%, 25%, or more). In some instances, a reduction in bilirubin level may be determined by measuring bilirubin levels according to a conventional in vivo method (e.g., blood analysis) and comparing the measured level to a predetermined threshold value or a baseline level of bilirubin measured just prior to the beginning of the treatment period.

The treatment period is ideally of sufficient time for the sucrose ester(s) present in the composition to reduce the bilirubin level of a target portion of skin. In some instances, the bilirubin reduction benefit provided by the sucrose ester may be demonstrated by a reduction in b* value relative to a predetermined b* value (i.e., a b* baseline value or threshold value). Additionally or alternatively, the bilirubin reduction benefit may be demonstrated by comparing a measured b* value and/or bilirubin level to a control value (e.g., vehicle control) or other reference value. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

METHODS

Bilirubin Degradation Assay

This assay provides an in vitro method of determining how a material or composition affects bilirubin degradation. Three replicates of each test sample are prepared in a 96-well plate (e.g., a FALCON brand 96-well tissue culture plate or equivalent) at a total volume of 250 μl/well. A stock of 250 ug/ml indirect bilirubin (i.e., the unconjugated form of bilirubin most commonly found in blood serum) is made by dissolving bilirubin powder (Cayman Chemicals Company, Catalog #17161) in DMSO (Sigma, Catalog #D8414-100 ml) to yield a stock solution at 10× working concentration. Working concentration of bilirubin is set at 25 ug/ml for every well except negative/vehicle control wells. Each test well contains 25 ul of 250 ug/ml bilirubin stock solution, 200 ul PBS and 25 ul of 10× treatment solution stock made in DMSO. For a 0.01% (w/v) sucrose ester treatment, a 10× concentrate stock is made at 0.1% (w/v) in DMSO. Of course, it is to be appreciated that the amount of DMSO can be adjusted depending on the solubility of the active (e.g., 80% or more DMSO for water insoluble actives such as the sucrose esters herein) to provide a stable solution for testing. For negative/vehicle control wells, DMSO is mixed with PBS to yield a final DMSO concentration that is the same as the test wells (e.g., 80% (v/v) or more). For positive control wells, 25 ul of 250 ug/ml bilirubin stock made in DMSO, 200 ul PBS (AccuGENE, Catalog #51225), and sufficient additional DMSO to yield a final DMSO concentration that is the same as the test wells.

The plate(s) containing the test samples are covered with aluminum foil and placed on top of a microplate shaker (VWR, Catalog #12620-938). Incubation is carried out at room temperature for 20-hr with constant shaking at 150 rpm. Bilirubin concentration is quantified after 20-hr incubation to determine the effect of bilirubin degradation as a result of active treatment in comparison to positive bilirubin control. Commercially available bilirubin quantification kit (Cell Biolab, Catalog #MET-5010) is used for bilirubin quantification. The assay is based on the Jendrassik-Grof method in which diazotized sulfanilic acid reacts with bilirubin to form azobilirubin, the latter of which can be detected at an OD of 540 nm. A standard bilirubin curve is generated using the same bilirubin used for treatment and quantified. Table 1 below provides a standard-curve setup.

TABLE 1

| Sample ID | Bilirubin concentration (ug/ml) | Making method |
| --- | --- | --- |
| Std1 | 200 | 300 ul of 500 ug/ml bilirubin stock in DMSO + 450 ul of PBS |
| Std2 | 100 | 300 ul of std1 + 300 ul of PBS |
| Std3 | 50 | 300 ul of std2 + 300 ul of PBS |
| Std4 | 25 | 300 ul of std3 + 300 ul of PBS |
| Std5 | 12.5 | 300 ul of std4 + 300 ul of PBS |
| Std6 | 5 | 300 ul of std5 + 450 ul of PBS |
| Std7 | 2.5 | 300 ul of std6 + 300 ul of PBS |
| Std8 | 0 | equal volume of PBS and DMSO |

Bilirubin concentrations of all testing legs are calculated using linear regression against the standard bilirubin curve. Bilirubin concentrations as a result of treatment are compared to positive bilirubin control leg. Bilirubin degradation activity can be confirmed by numerical reduction of bilirubin quantification of treatment leg vs. bilirubin positive control leg with P<0.05 using paired student t-test.

EXAMPLES

Example 1: Formulations

Table 2 below provides examples of topical skin care compositions comprising a sucrose ester. The exemplary compositions are made by blending the A phase components with a suitable mixer (e.g., Tekmar RW20DZM or equivalent) and heating to a temperature of 70-80° C. and maintaining the temperature while stirring. Separately, the B phase components are blended with a suitable mixer and heated to 70-75° C., while maintaining temperature during mixing. Phase B is added to Phase A while mixing well to form an oil-in-water (O/W) emulsion. The emulsion is then milled using a suitable mill (e.g., Tekmar T-25 or equivalent) for 5 minutes. When the emulsion is at 60° C., phase C is added while continuing to mix. At 40° C., the ingredients of phase D and E are added to the emulsion. The emulsion is then milled for 5 minutes to provide a uniform composition.

included 0.01% and 0.05% sucrose ester (BC10034 from BASF). The plate(s) containing the test compositions were

TABLE 2

Exemplary formulation

| Component | I | II | III | IV | V | VI | VII | VIII | IX |
|---|---|---|---|---|---|---|---|---|---|
| Phase A | | | | | | | | | |
| Water | qs | qs | qs | qs | qs | qs | qs | qs | qs |
| Glycerol | 5.00 | 7.00 | 3.00 | 15.0 | 7.00 | 5.00 | 5.00 | 3.00 | 5.00 |
| Disodium EDTA | 0.10 | 0.05 | 0.10 | 0.10 | 0.05 | 0.05 | 0.05 | 0.05 | 0.10 |
| Phase B | | | | | | | | | |
| Dimethicone 5 cSt | — | — | — | — | — | — | — | 10.0 | 15.0 |
| Dimethicone and Dimethicone Crosspolymer[1] | — | — | — | — | — | — | — | 13.0 | 15.0 |
| Laureth-4 | — | — | — | — | — | — | — | 0.25 | 0.35 |
| Polysorbate 20 | — | — | — | — | — | — | — | 0.15 | 0.25 |
| Tapioca Starch and Polymethylsilsesquioxane[2] | — | — | — | — | — | — | — | 2.50 | 3.50 |
| Avobenzone | — | — | — | 3.00 | — | 3.00 | — | — | — |
| Homosalate | — | — | — | 15.0 | — | 10.0 | — | — | — |
| Octisalate | — | — | — | 5.00 | — | 5.00 | — | — | — |
| Octocrylene | — | — | — | 2.60 | — | 9.00 | — | — | — |
| Isopropyl Isostearate | 5.00 | 2.50 | 1.00 | — | — | — | — | — | — |
| Isohexadecane | 1.00 | 1.50 | 3.00 | — | — | — | — | — | — |
| Cetyl Alcohol | 0.25 | 0.50 | 0.32 | 0.40 | 0.40 | 0.30 | 0.50 | — | — |
| Tocopherol Acetate | | 0.50 | 0.25 | 1.00 | 0.25 | 0.25 | 0.25 | — | — |
| PEG-100 Stearate | 0.20 | 0.10 | 0.10 | 0.30 | 0.10 | 0.20 | 0.10 | — | — |
| Stearyl Alcohol | 0.50 | 1.50 | 0.40 | 0.60 | 0.50 | 0.40 | 0.60 | — | — |
| Behenyl Alcohol | 0.40 | 1.00 | 0.50 | 0.50 | 0.40 | 0.35 | 0.50 | — | — |
| Ethyl Paraben | 0.20 | 0.15 | 0.20 | 0.25 | — | — | — | — | — |
| Propyl Paraben | 0.10 | 0.15 | 0.10 | 0.15 | — | — | — | — | — |
| Polymethylsilsesquioxane | 1.25 | 2.50 | 1.00 | — | — | — | — | — | — |
| Phase C | | | | | | | | | |
| Titanium Dioxide | — | 0.50 | — | 0.25 | — | — | — | — | — |
| Tapioca Starch and Polymethylsilsesquioxane[2] | — | — | — | — | — | 12.0 | — | — | — |
| Vinyl Dimethicone/Methicone Silsesquioxane Crosspolymer[3] | 1.50 | — | 1.50 | 3.50 | 5.00 | — | 7.50 | — | — |
| Sodium Polyacrylate Starch[4] | — | — | — | — | 1.50 | 1.00 | 1.50 | — | — |
| Hydroxyethyl acrylate/sodium acryloyldimethyltaurate copolymer[5] | 2.00 | 1.50 | 2.50 | 2.00 | — | — | — | 1.25 | 2.00 |
| Phase D | | | | | | | | | |
| Water | 5.00 | 10.0 | 10.0 | 5.00 | 10.0 | 10.0 | 10.0 | 5.00 | 10.0 |
| Sucrose ester[6] | 0.25 | 0.40 | 3.50 | 0.40 | 0.1 | 1.25 | 1.00 | 1.00 | 5.00 |
| Niacinamide | 1.00 | | 3.50 | | 2.00 | 5.00 | | — | 1.00 |
| Dexpanthenol | 0.25 | 0.50 | 0.50 | 1.00 | 1.00 | 1.50 | 0.25 | 1.00 | 0.50 |
| Phase E | | | | | | | | | |
| Benzyl alcohol | 0.25 | 0.40 | 0.25 | 0.50 | — | — | — | — | — |
| Hexanediol and Caprylyl Glycol[7] | — | — | — | — | 0.70 | 0.80 | 0.70 | 0.70 | 1.00 |
| Phenoxyethanol | — | — | — | — | 0.3 | 0.4 | 0.5 | 0.20 | 0.25 |
| Dimethicone/dimethiconol | 0.5 | 1.00 | 2.00 | 1.00 | 2.00 | 2.00 | 1.00 | 1.75 | 1.00 |

1. DOWSIL available from Dow Chemical.
2. DRYFLO TS available from Nouryon.
3. KSP-100 available from Shin-Etsu.
4. MAKIMOUSSE-25 available from Kobo Products.
5. SIMULGEL INS available from Seppic.
6. BC10034 from BASF.
7. SYMDIOL 68 available from Symrise.
8. XIAMETER PMX-1503 available from Dow Corning.

Example 2: Sucrose Ester Provides a Bilirubin Degradation Benefit

This example demonstrates the ability of a sucrose ester to reduce yellowness attributed to insoluble bilirubin in a dose-dependent manner Test compositions and control compositions were prepared as described above in the Bilirubin Degradation Assay. The two test compositions respectively covered with aluminum foil and placed on top of a microplate shaker (VWR, Catalog #12620-938). Incubation was carried out at room temperature for 20-hr with constant shaking at 150 rpm. Yellowness (b*) was determined by measuring the absorbance of the samples in 10 nm increments from 350 nm to 750 nm using a suitable spectrophotometer as follows (the b* assay). Absorbance was measured in triplicate at T=0 (i.e., immediately after plate set up) and after 20 hours of incubation. The absorbance spectrum from the yellowness measurement was then converted to L*a*b* values by a computer using conversion software. The results of the analysis are summarized in Table 3 and illustrated in FIG. 1. As can be seen in Table 3 and FIG. 1, the sucrose ester reduced yellowness (b*) by a statistically significant amount relative to the positive control. The skin care compositions herein may include an effective amount of sucrose ester to reduce b* value by at least 10% (e.g., at least 15%, 20%, 25%, 30%, 35%, 40%, 50%, or more) relative to a vehicle control.

TABLE 3

Sucrose ester yellowness benefit

|  | b* initial | b* 20 hours |
|---|---|---|
| Vehicle | 0.1 | 0.2 |
| Positive Control | 97.92 | 90.48 |
| 0.01% | 84.01 | 65.17 |
| 0.05% | 74.52 | 60.44 |

Figure 2:
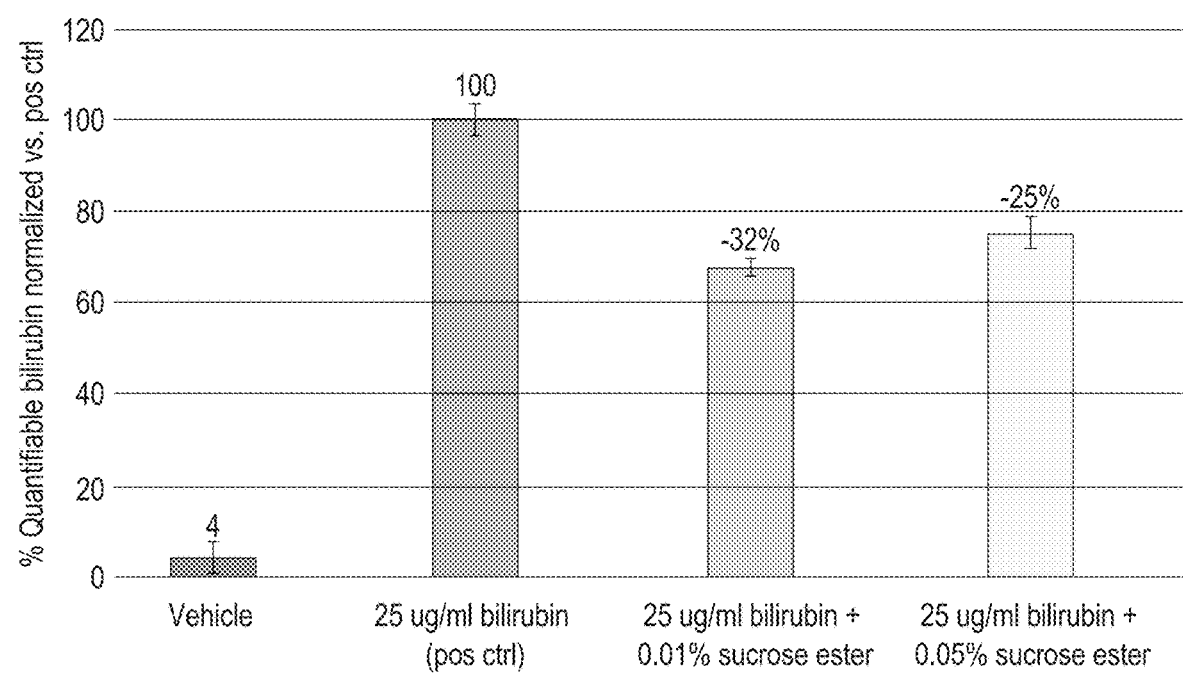
FIG. 2 illustrates the in vitro effects of a sucrose ester on bilirubin level.

The test samples were also analyzed after the 20-hr incubation to determine the amount of bilirubin that degraded as a result of treatment with the sucrose ester. The bilirubin amount was quantitated according to the Bilirubin Degradation Assay. The results of this analysis are illustrated in FIG. 2, which shows that the sucrose ester reduced bilirubin levels relative to the positive control. In some instances, it may be desirable to formulate a skin care composition to include an amount of sucrose ester that reduces bilirubin levels by at least 10% (e.g., at least 15%, 20%, 25%, 30%, 35%, 40%, 50%, or more) relative to a positive control.

It is noted that the 0.01% (w/v) sucrose ester test leg provided better bilirubin reduction than the 0.05% (w/v) sucrose ester test leg, which is unexpected. One would typically expect a dose response in which a higher concentration of sucrose ester provides better bilirubin degradation than a lower concentration. However, it is believed, without being limited by theory, that the atypical dose response observed in this example is due to the insolubility of sucrose ester in the 20% DMSO solution. Indeed, higher concentrations of sucrose ester appear to cause the sucrose ester to "crash out" out of solution, thereby reducing the efficacy of the test composition. Increasing the amount of DMSO in the test composition (e.g., to 80% (v/v) or more) should result in the expected dose response curve.

Example 3: Clinical Study

This example demonstrates the ability of a 1% sucrose ester composition to provide improved bilirubin degradation over the course of a treatment period. A test composition containing 1% sucrose ester was tested in an 8-week trial involving 336 female test subjects (aged 25-55 years). The test was arranged as a split face, randomized, vehicle controlled round robin design with 96 observations per test leg. During the study, some of the test subjects applied a 1% sucrose ester test composition to one side of their face and a vehicle control to the other side. The test composition is shown in Table 4 below. The test composition and vehicle control were formulated using conventional methods for making oil-in-water emulsion-type skin care compositions.

TABLE 4

Test Composition

| Ingredient | wt % |
|---|---|
| Water | qs |
| Glycerine | 10.00 |
| EDTA | 0.10 |
| Tocopheryl acetate | 0.50 |
| Isopropyl isostearate | 1.33 |
| Sefa cottonate | 0.67 |
| 1,2-pentanediol | 3.00 |
| Polymethylsilsequioxane | 0.25 |
| Cetearyl glucoside and cetearyl alcohol | 0.20 |
| Behenyl alcohol | 0.40 |
| Ethylparaben | 0.20 |
| Propylparaben | 0.10 |
| Cetyl alcohol | 0.32 |
| Stearyl alcohol | 0.48 |
| PEG-100 stearate | 0.10 |
| Polyacrylamide, C13-14 isoparafin, laureth-7 | 2.50 |
| Dexpanthenol | 1.00 |
| Benzyl alcohol | 0.25 |
| Dimethiconol | 2.00 |
| Sucrose ester[1] | 1.00 |

[1]BC10034 from BASF

Figure 3:
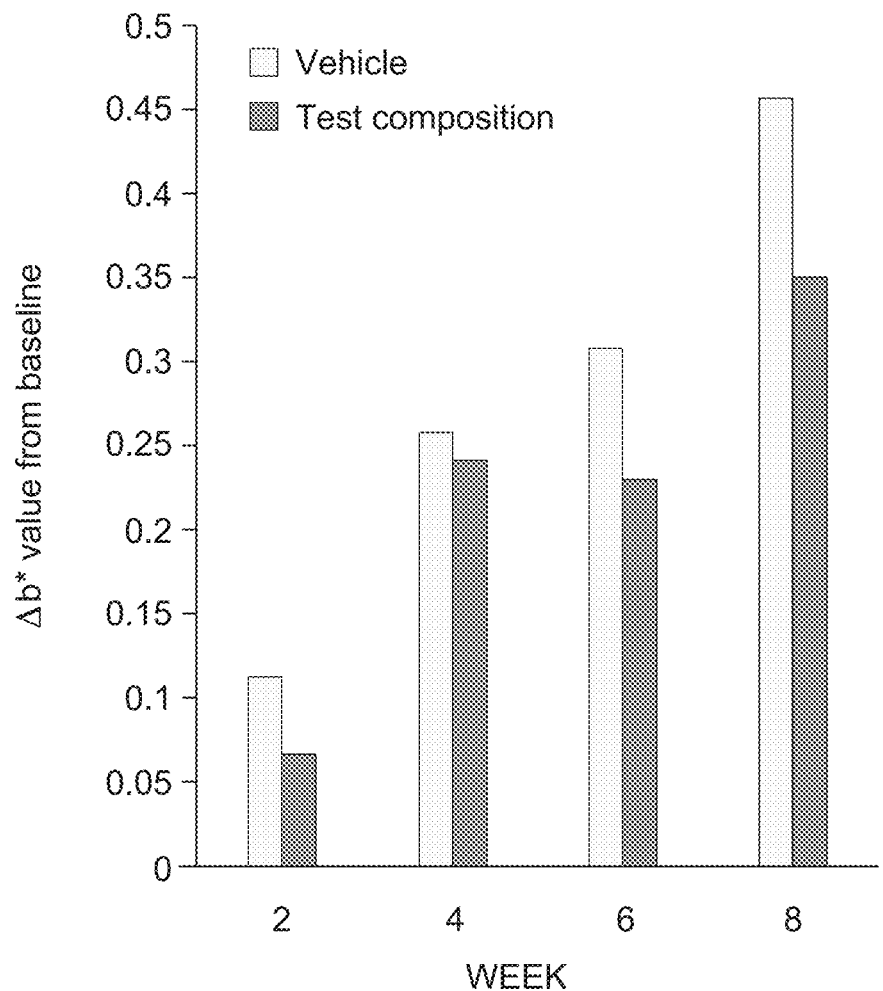
FIG. 3 illustrates the in vivo effects of a sucrose ester composition on skin yellowness.

A Rapid Evaluation of Anti-aging Leads (REAL) image analysis system was used to capture and analyze digital images of each test subject's face on a biweekly basis to determine b* value. The REAL image analysis system is described by Miyamoto, et al., in "Development of a Digital Imaging System for Objective Measurement of Hyperpigmented Spots on the Face;" Skin Res Technol 2002; 8:227-35. The results of the clinical study are summarized in Table 5 below and illustrated in FIG. 3. A p-value of 0.1 or less is considered statistically significant. As can be seen in Table 5 and FIG. 3, the test composition significantly inhibits the increase in skin yellowness compared to the vehicle control after 6 weeks of use.

TABLE 5

| | b* value | | |
|---|---|---|---|
| Week | Vehicle | Test Composition (1% SD) | p-value |
| 0 | 0 | 0 | — |
| 2 | 0.113 | 0.067 | >0.1 |
| 4 | 0.229 | 0.243 | >0.1 |
| 6 | 0.308 | 0.231 | <0.1 |
| 8 | 0.458 | 0.350 | <0.05 |

It is noted that b* value appears to increase over the course of the study, albeit less so for the test composition. It is believed, without being limited by theory, that the increase in b* value is because the study was conducted in summer. It is well-known that increased sun intensity and sun exposure, which is common in summer, tend to increase melanin production in skin and higher melanin levels result in higher b* values. Thus, it appears that the increasing melanin levels associated with summertime sun exposure of the test subjects caused higher b* value to increase over the course of the 8-week study. However, the test subjects who used the test composition had less b* increase relative to the vehicle control, which demonstrates the effectiveness of the test composition.

Example 4: Correlating Bilirubin Concentration to Yellowness

It is believed, without being limited by theory, that bilirubin concentration in skin has a direct correlation to a yellow or sallow skin appearance. To determine the correlation between bilirubin concentration and yellowness, a bilirubin standard curve is generated. Bilirubin powder (Cayman Chemicals Company, Catalog #17161) is dissolved in DMSO (Sigma, Catalog #D8414-100 ml) to make a 500 ug/ml bilirubin stock. This bilirubin stock is diluted in PBS as shown in Table 1 above to yield bilirubin levels at 50, 25, 12.5, 5, 2.5, and 0 ug/ml. To measure yellowness ($b^*$), the samples are loaded into a 96-well plate in triplicate and the absorbance of each sample is measured in 10 nm increments from 350 nm to 750 nm using a suitable spectrophotometer. The absorbance spectrum from the yellowness measurement are then converted to $L^*a^*b^*$ values by a computer using suitable conversion software.

Figure 4:
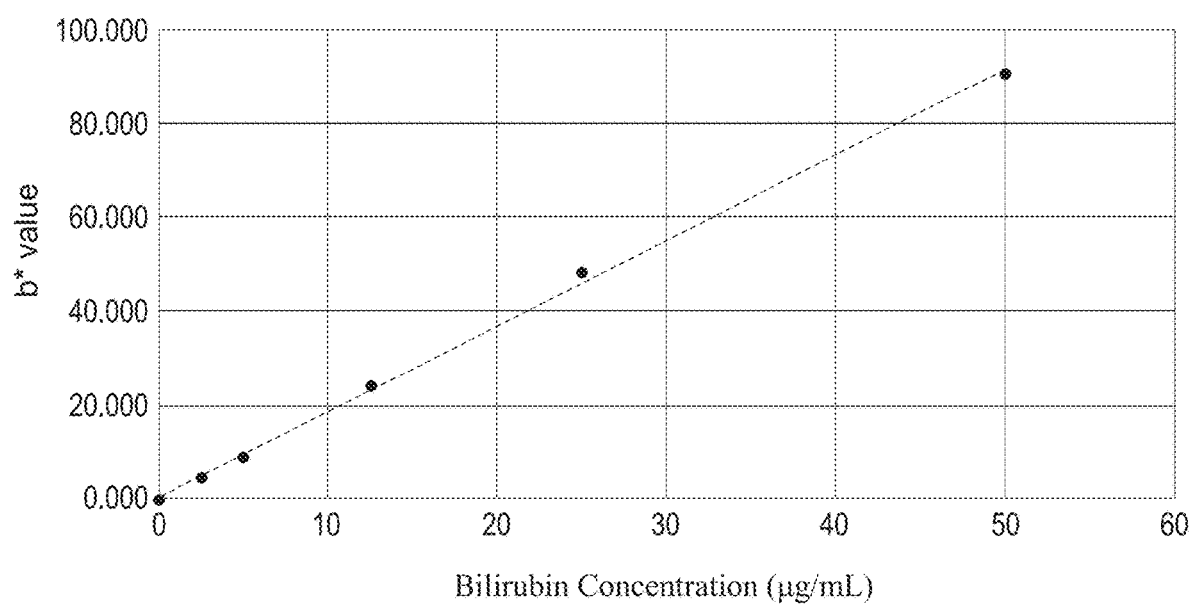
FIG. 4 illustrates the direct correlation between bilirubin level and b* value.

As shown in Table 6 and FIG. 4, the $b^*$ scores show a linear correlation to bilirubin concentration in the range of 0 ug/ml to 50 ug/ml bilirubin. Human biological bilirubin concentration falls within this concentration range. Thus, the data show that bilirubin concentration in skin has a direct correlation to a sallow appearance.

TABLE 6

| Bilirubin Concentration (µg/mL) | Average $b^*$ value |
|---|---|
| 0 | −0.417 |
| 2.5 | 4.258 |
| 5 | 8.582 |
| 12.5 | 23.889 |
| 25 | 47.993 |
| 50 | 90.017 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition, comprising:
   a) an effective amount of sucrose ester comprising sucrose laurate and sucrose dilaurate at a ratio of sucrose laurate to sucrose dilaurate ranging from about 3:1 to about 3:2 wherein the effective amount of sucrose ester reduces yellowness levels according to a $b^*$ assay by at least 10% relative to a vehicle control containing the dermatologically acceptable carrier without sucrose ester; and
   b) a dermatologically acceptable carrier.

2. The skin care composition of claim 1, wherein the sucrose ester is present at about 0.001% to about 10% by weight of the composition.

3. The skin care composition of claim 1, wherein the composition further comprises at least one additional ingredient selected from vitamins, minerals, peptides, sugar amines, sunscreen agents, oil control agents, flavonoid compounds, anti-oxidants, preservatives, protease inhibitors, tyrosinase inhibitors, anti-inflammatory agents, moisturizing agents, exfoliating agents, skin lightening agents, lubricants, anti-acne actives, chelating agents, anti-wrinkle actives, anti-atrophy actives, phytosterols, N-acyl amino acid compounds, antimicrobials, and antifungals, conditioning agents, emulsifiers, rheology modifiers, and combinations thereof.

4. The skin care composition of claim 3, wherein the additional ingredient is selected from vitamin B3 compounds, vitamin E compounds, peptides, retinoids, and combinations thereof.

5. The skin care composition of claim 3, wherein the additional ingredient includes a rheology modifier selected from sodium polyacrylate superabsorbent polymers, starch grafted sodium polyacrylate superabsorbent polymers, and combinations thereof.

6. The skin care composition of claim 1, further comprising at least about 10% of a silicone fluid.

7. The skin care composition of claim 1, wherein the skin care composition is an oil-in-water emulsion.

8. The skin care composition of claim 7, further comprising a non-ionic emulsifier.

9. A method of degrading bilirubin in skin, comprising:
   a) identifying a target portion of skin where treatment is desired; and
   b) applying the skin care composition of claim 1 to the target portion of skin, wherein the effective amount of sucrose ester reduces yellowness levels over the course of a treatment period.

10. The method of claim 9, wherein the composition comprises about 0.001% to about 10% sucrose ester, by weight.

11. The method of claim 9, wherein the target portion of skin exhibits a sign of bilirubin accumulation.

12. The method of claim 9, wherein the effective amount of sucrose ester reduces $b^*$ value by at least 10% relative to the vehicle control, according to the $b^*$ assay.

13. The method of claim 9, wherein the effective amount of sucrose ester reduces yellowness levels by at least 10% relative to a positive control of 80% (v/v) bilirubin in dimethyl sulfoxide, according to the $b^*$ assay.

14. The method of claim 9, wherein the treatment period is at least 2 weeks.

15. The method of claim 9, wherein the composition includes at least about 10% of a silicone fluid.

16. The method of claim 9, wherein the composition further comprises at least one additional ingredient selected from vitamins, minerals, peptides, sugar amines, sunscreen agents, oil control agents, flavonoid compounds, anti-oxidants, preservatives, protease inhibitors, tyrosinase inhibitors, anti-inflammatory agents, moisturizing agents, exfoliating agents, skin lightening agents, lubricants, anti-acne actives, chelating agents, anti-wrinkle actives, anti-atrophy actives, phytosterols, N-acyl amino acid compounds, antimicrobials, and antifungals, conditioning agents, emulsifiers, rheology modifiers, and combinations of these.

17. The method of claim 16, wherein the additional ingredient is selected from vitamin B3 compounds, vitamin E compounds, peptides, retinoids, and combinations thereof.

* * * * *